(12) United States Patent
Wang et al.

(10) Patent No.: US 6,750,258 B2
(45) Date of Patent: *Jun. 15, 2004

(54) CATALYST STRUCTURE AND METHOD OF FISCHER-TROPSCH SYNTHESIS

(75) Inventors: Yong Wang, Richland, WA (US); David P. Vanderwiel, Richland, WA (US); Anna Lee Y. Tonkovich, Pasco, WA (US); Yufei Gao, Kennewick, WA (US); Eddie G. Baker, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/282,554

(22) Filed: Oct. 28, 2002

(65) Prior Publication Data

US 2003/0149120 A1 Aug. 7, 2003

Related U.S. Application Data

(60) Division of application No. 09/492,245, filed on Jan. 27, 2000, now Pat. No. 6,491,880, which is a continuation-in-part of application No. 09/375,610, filed on Aug. 17, 1999, now Pat. No. 6,451,864.

(51) Int. Cl.$^7$ ............................................... C07C 27/00
(52) U.S. Cl. ....................................... 518/715; 518/700
(58) Field of Search ................................. 518/700, 715

(56) References Cited

U.S. PATENT DOCUMENTS

| | | | |
|---|---|---|---|
| 3,581,489 A | 6/1971 | Clamin et al. ................. 60/300 |
| 3,998,758 A | 12/1976 | Clyde ........................... 502/307 |
| 4,062,808 A | 12/1977 | Gandhi et al. ................. 252/454 |
| 4,196,099 A | 4/1980 | Hunter et al. ................. 252/437 |
| 4,422,961 A | 12/1983 | Gray ............................ 502/301 |
| 4,472,533 A | 9/1984 | Moskovits ..................... 502/320 |
| 4,738,948 A | 4/1988 | Iglesia et al. ................. 502/326 |
| 4,748,145 A | * 5/1988 | Wood et al. .................. 502/332 |
| 4,801,620 A | 1/1989 | Fujitani et al. ............... 518/715 |
| 4,806,427 A | 2/1989 | Stein et al. ................... 502/60 |
| 4,935,392 A | 6/1990 | Kainer et al. ................. 502/60 |
| 4,945,116 A | 7/1990 | Abrevaya ..................... 518/715 |
| 4,975,406 A | 12/1990 | Frestad et al. ............... 502/302 |
| 4,985,230 A | 1/1991 | Baden et al. ................. 423/650 |
| 5,023,276 A | 6/1991 | Yarrington et al. .......... 514/703 |
| 5,227,407 A | 7/1993 | Kim ............................. 518/700 |
| 5,366,719 A | 11/1994 | van Wingerden et al. .. 423/659 |
| 5,422,331 A | 6/1995 | Galligan et al. ............. 502/333 |
| 5,440,872 A | 8/1995 | Pfefferle ..................... 60/39.06 |
| 5,461,022 A | 10/1995 | Dosch et al. ................ 502/242 |
| 5,545,674 A | 8/1996 | Behrmann et al. .......... 518/715 |
| 5,565,009 A | 10/1996 | Ruhl et al. .................. 48/197 R |
| 5,652,193 A | 7/1997 | Herskowitz ................. 502/332 |
| 5,766,458 A | 6/1998 | Sekhar et al. ............... 210/184 |
| 5,866,734 A | 2/1999 | Flick et al. .................. 585/260 |
| 5,935,533 A | 8/1999 | Kleefisch et al. ........... 422/211 |
| 6,211,255 B1 | 4/2001 | Schanke et al. ............ 518/715 |
| 6,262,131 B1 | 7/2001 | Arcuri et al. ............... 518/700 |
| 6,440,895 B1 * | 8/2002 | Tonkovich et al. ......... 502/439 |
| 6,451,864 B1 | 9/2002 | Wang et al. ................ 518/715 |
| 6,491,880 B1 | 12/2002 | Wang et al. ................ 422/211 |
| 6,558,634 B1 | 5/2003 | Wang et al. ................ 422/173 |

FOREIGN PATENT DOCUMENTS

RU  2093261  10/1997  ......... B01J/23/755

OTHER PUBLICATIONS

Pestrykov et al., "Foam Metal Catalysts With Intermediate Support For Deep Oxidation Of Hydrocarbons," React. Kinet. Catal. Lett., vol. 53, pp. 347–352 (1994).
Dixit et al., "Kinetics of the Fischer–Tropsch Synthesis," Ind. Eng. Chem. Process Dev., 1983, 1–9.
Everson et al., "Fischer–Tropsch Reaction Studies with Supported Ruthenium Ctalysts," J. Catal. 53, 186–197 (1978).
Franz et al., "New Operating Regimes and Applications Feasible with Microreactors," Process Mini.: 2nd Intl Conf. On MicroTech, 33–38 (1998).
Weissmeier et al., "Strategy for the Development of Micro Channel Reactors for Heterogeneously Catalyzed Reactions," Process Mini.: 2nd Intl Conf. On Micro Tech, 24–32, (1998).
Twigg et al., "Metal and Coated Metal Catalysts," Chapter 3, pp 59–90.

* cited by examiner

Primary Examiner—J. Parsa
(74) Attorney, Agent, or Firm—Frank Rosenberg; Todd J. Harrington

(57) ABSTRACT

The present invention includes Fischer-Tropsch catalysts, reactions using Fischer-Tropsch catalysts, methods of making Fischer-Tropsch catalysts, processes of hydrogenating carbon monoxide, and fuels made using these processes. The invention provides the ability to hydrogenate carbon monoxide with low contact times, good conversion rates and low methane selectivities. In a preferred method, the catalyst is made using a metal foam support.

12 Claims, 2 Drawing Sheets

CATALYST STRUCTURE AND METHOD OF FISCHER-TROPSCH SYNTHESIS

RELATED APPLICATIONS

This application is a divisional of U.S. Ser. No. 09/492,245, filed Jan. 27, 2000 now U.S. Pat. No. 6,491,880, which was a continuation-in-part of U.S. Ser. No. 09/375,610, filed Aug. 17, 1999, now U.S. Pat. No. 6,451,864, which is incorporated by reference.

This invention was made with Government support under Contract DE-AC0676RLO1830 awarded by the U.S. Department of Energy. The Government has certain rights in the invention.

FIELD OF THE INVENTION

The present invention is a catalyst structure and method of making, and a method of Fischer-Tropsch synthesis.

BACKGROUND OF THE INVENTION

Fischer-Tropsch synthesis is carbon monoxide hydrogenation that is usually performed on a product stream from another reaction including but not limited to steam reforming (product stream $H_2/CO\sim3$), partial oxidation (product stream $H_2/CO\sim2$), autothermal reforming (product stream $H_2/CO\sim2.5$), $CO_2$ reforming ($H_2/CO\sim1$) coal gassification (product stream $H_2/CO\sim1$) and combinations thereof.

Fundamentally, Fischer-Tropsch synthesis has fast surface reaction kinetics. However, the overall reaction rate is severely limited by heat and mass transfer with conventional catalysts or catalyst structures. The limited heat transfer together with the fast surface reaction kinetics may result in hot spots in a catalyst bed. Hot spots favor methanation. In commercial processes, fixed bed reactors with small internal diameters or slurry type and fluidized type reactors with small catalyst particles (>50 microns, $\mu m$) are used to mitigate the heat and mass transfer limitations. In addition, one of the important reasons that Fischer-Tropsch reactors are operated at lower conversions per pass is to minimize temperature excursion in the catalyst bed. Because of the necessary operational parameters to avoid methanation, conventional reactors are not improved even with more active Fischer-Tropsch synthesis catalysts. Detailed operation is summarized in Table 1 and FIG. 1.

TABLE 1

Comparison of Contact Times Effects in Fischer-Tropsch Experimentation

| Ref[A] | Catalyst | Conditions | Contact time | Conversion | $CH_4$ selectivity |
|---|---|---|---|---|---|
| 1 | Co/ZSM-5 | 240° C., 20-atm, $H_2/CO$ = 2 | 3.6-sec | 60% | 21% |
| 2 | Co/MnO | 220° C., 21-atm, $H_2/CO$ = 2 | 0.72-sec | 13% | 15% |
| 3 | Co—Ru/$TiO_2$ | 200° C., 20-atm, $H_2/CO$ = 2 | 3-sec | 61% | 5% |
|  | Co/$TiO_2$ | " | 8-sec | 49% | 7% |
| 4 | Co/$TiO_2$ | 200° C., 20-atm, $H_2/CO$ = 2.1 | 2-sec | 9.5% | ~9% |
|  |  |  | 12-sec | 72% | ~6% |
| 5 | Ru/$Al_2O_3$ | 222° C., 21-atm, $H_2/CO$ = 3 | 4.5-sec | 20% | ? |
|  |  | " | 7.2-sec | 36% |  |
|  |  | " | 8.4-sec | 45% |  |
|  |  | " | 9.6-sec | 51% |  |
|  |  | " | 12-sec | 68% |  |
|  |  | " | 14-sec | 84% |  |
| 6 | Ru/$Al_2O_3$ | 250° C., 22-atm, $H_2/CO$ = 2 | 7.2-sec | 38% | 5% |
| 7 | Ru/$Al_2O_3$ | 225° C., 21-atm, $H_2/CO$ = 2 | 12-sec | 66% | 13% |
|  |  | 222° C., 21-atm, $H_2/CO$ = 3 | 12-sec | 77% | 34% |

For references that contained results for multiple experimental conditions, the run which best matched our conversion, selectivity and/or conditions was chosen for comparison of contact time.

[A]References
1. Bessell, S., Appl. Catal. A: Gen. 96, 253 (1993).
2. Hutchings, G. J., Topics Catal. 2, 163 (1995).
3. Iglesia, E., S. L. Soled and R. A. Fiato (Exxon Res. and Eng. Co.), U.S. Pat. No. 4,738,948, Apr. 19, 1988.
4. Iglesia, E., S. C. Reyes, R. J. Madon and S. L. Soled, Adv. Catal. 39, 221 (1993).
5. Karn, F. S., J. F. Shultz and R. B. Anderson, Ind Eng. Chem. Prod. Res. Dev. 4(4), 265 (1965).
6. King, F., E. Shutt and A. I. Thomson, Platinum Metals Rev. 29 (44), 146 (1985).
7. Shultz, J. F., F. S. Karn and R. B. Anderson, Rep. Invest. - U.S. Bur. Mines 6974, 20 (1967).

Literature data (Table 1 and FIG. 1) were obtained at lower $H_2/CO$ ratio (2:1) and longer contact time (3 sec or longer) in a fixed bed type reactor. Low $H_2/CO$ (especially 2–2.5), long contact time, low temperature, and higher pressure favor Fischer-Tropsch synthesis. Selectivity to $CH_4$ is significantly increased by increasing $H_2/CO$ ratio from 2 to 3. Increasing contact time also has a dramatic favorable effect on the catalyst performance. Although reference 3 in Table 1 shows satisfactory results, the experiment was conducted under the conditions where Fischer-Tropsch synthesis is favored (at least 3 sec residence time, and $H_2/CO$= 2). In addition, the experiment of reference 3 was done using a powdered catalyst on an experimental scale that would be impractical commercially because of the pressure drop penalty imposed by powdered catalyst. Operating at higher temperature will enhance the conversion, however at the much higher expense of selectivity to $CH_4$. It is also noteworthy that contact time in commercial Fischer-Tropsch units is at least 10 sec.

Hence, there is a need for a catalyst structure and method of Fischer-Tropsch synthesis that can achieve the same or higher conversion at shorter contact time, and/or at higher $H_2/CO$.

SUMMARY OF THE INVENTION

The present invention includes a catalyst structure and method of making the catalyst structure for Fischer-Tropsch synthesis that have a first porous structure with a first pore surface area and a first pore size of at least about 0.1 $\mu$m, preferably from about 10 $\mu$m to about 300 $\mu$m. A porous interfacial layer with a second pore surface area and a second pore size less than the first pore size disposed on the first pore surface area. A Fischer-Tropsch catalyst selected from the group consisting of cobalt, ruthenium, iron, nickel, rhenium, osmium and combinations thereof is placed upon the second pore surface area.

The present invention also provides a method of making a Fischer-Tropsch catalyst having the steps of: providing a catalyst structure comprising a porous support with a first pore surface area and a first pore size of at least about 0.1 $\mu$m; optionally depositing a buffer layer on the porous support; depositing a porous interfacial layer with a second pore surface area and a second pore size less than said first pore size, upon the buffer layer (if present); and depositing a Fischer-Tropsch catalyst upon the second pore surface area.

The present invention further includes a method of Fischer-Tropsch synthesis having the steps of:

providing a catalyst structure having a first porous support with a first pore surface area and a first pore size of at least about 0.1 $\mu$m;

a buffer layer disposed on the porous support;

a porous interfacial layer with a second pore surface area and a second pore size less than the first pore size, the porous interfacial layer disposed on the buffer layer (if present) or on the first pore surface area; and a Fischer-Tropsch catalyst disposed on the second pore surface area; and (b) passing a feed stream having a mixture of hydrogen gas and carbon monoxide gas through the catalyst structure and heating the catalyst structure to at least 200° C. at an operating pressure, the feed stream having a residence time within the catalyst structure less than 5 seconds, thereby obtaining a product stream of at least 25% conversion of carbon monoxide, and at most 25% selectivity toward methane.

The present invention also includes various supported Fischer-Tropsh catalysts that are characterized by their properties. For example, a catalyst is provided that, if exposed to a feed stream consisting of a 3 to 1 ratio of hydrogen gas to carbon monoxide, at 250° C. and a residence time of 12.5 seconds, exhibits a selectivity to methane that is greater at 24 atmospheres (contact time of 1 second) than it is at 6 atmospheres pressure (contact time of 4 seconds), even though the conversion is higher at lower pressure.

Catalytic activity is an intrinsic property of a catalyst. In the present invention, this property is defined by various testing conditions. For example, a preferred catalyst has a Fischer-Tropsch catalytic metal supported on a porous support; where the catalyst possesses catalytic activity such that, if the catalyst is placed in a tube inside an isothermal furnace and exposed to a feed stream consisting of a 3 to 1 ratio of hydrogen gas to carbon monoxide, at 250° C., at 6 atm, at a contact time less than 5 seconds and the product stream is collected and cooled to room temperature, the selectivity to methane is less than 25%, and the carbon monoxide conversion is greater than 25%. To check whether a catalyst meets a claimed activity property requires only a test at the specified conditions.

The invention also provides a method for hydrogenating carbon monoxide, in which a feed stream containing hydrogen and carbon monoxide is passed into a reaction chamber that contains a catalyst at a temperature of at least 200° C.; the catalyst having a supported Fischer-Tropsch catalytic metal; and collecting a product stream. In this process, heat is transferred from the reaction chamber at a sufficient rate such that, under steady-state conditions, the feed stream has: a contact time of less than about 2 seconds; a production rate of at least 1 milliliter per minute of liquid product where the liquid product is measured at 20° C. and 1 atm or at least 1 liter per minute of gaseous hydrocarbon product of molecules having at least 2 carbon atoms; a methane selectivity of less than 25%, and a carbon monoxide conversion greater than 25%. The hydrocarbons can be saturated, unsaturated or partially oxidized; and for use as fuels are preferably saturated hydrocarbons.

The present invention further includes reactors that use any of the catalysts described herein. The invention also includes hydrocarbon fuels made by any of the methods described herein. The present invention further includes methods of hydrogenating carbon monoxide that use any of the catalysts described herein.

Advantages that may be provided by the invention include (i) at residence/contact times shorter than the prior art, higher conversions are achieved with no increase to methane selectivity; and (ii) as residence/contact times increase, conversion increases and methane selectivity decreases. Surprisingly, it has been found that carbon monoxide can be hydrogenated at short contact time to produce liquid fuels at good conversion levels, low methane selectivities and good production rates.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
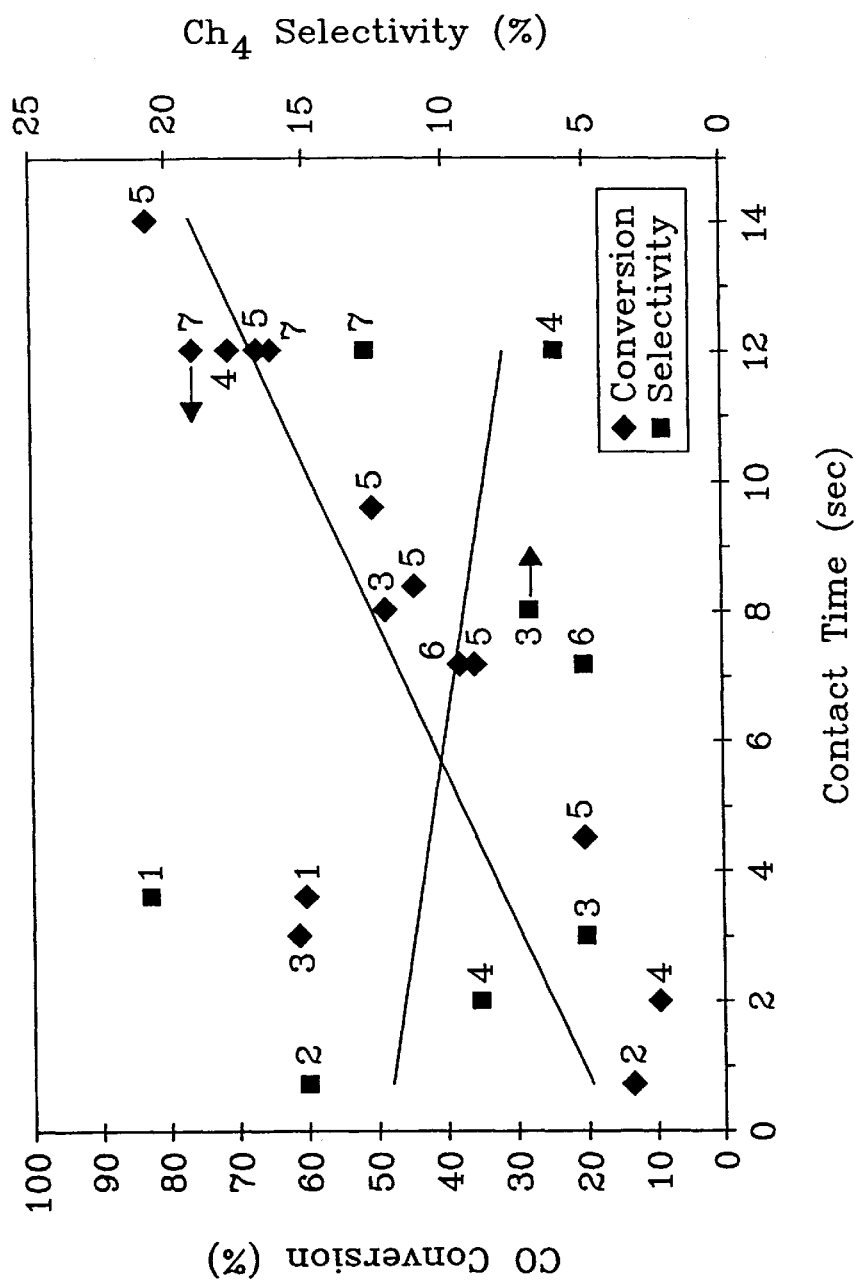
FIG. 1 is a graph of CO conversion versus contact time for prior art Fischer-Tropsch processes.
Figure 2:
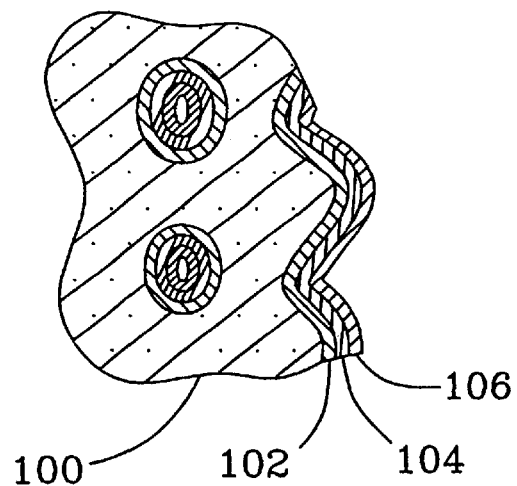
FIG. 2 is a cross section of a catalyst structure according to the present invention.
Figure 3:
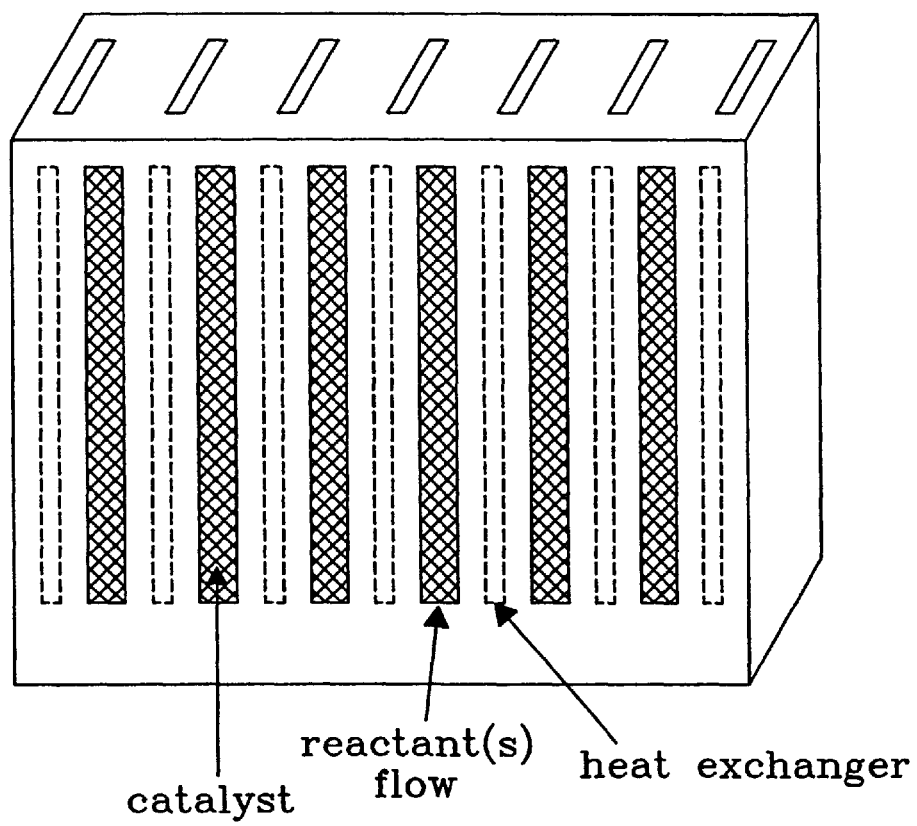
FIG. 3 illustrates a reactor design having multiple reaction chambers, each containing a catalyst, and multiple heat exchangers.

A catalyst of the present invention is depicted in FIG. 2 having a porous support 100, a buffer layer 102, an interfacial layer 104, and, optionally, a catalyst layer 106. Any layer may be continuous or discontinuous as in the form of spots or dots, or in the form of a layer with gaps or holes.

The porous support 100 may be a porous ceramic or a porous metal. Porous supports suitable for use in the present invention include carbides, nitrides, and composite materials. Prior to depositing the layers, the porous support preferably has a porosity of about 30% to about 99%, more preferably 60% to 98%, as measured by mercury porosimetry and an average pore size of from 1 $\mu$m to 1000 $\mu$m as measured by optical and scanning electron microscopy. Preferred forms of porous supports are foams, felts, wads and combinations thereof. Foam is a structure with continuous walls defining pores throughout the structure. Felt is a structure of fibers with interstitial spaces therebetween. Wad is a structure of tangled strands, like steel wool. Less preferably, porous supports may also include other porous media such as pellets and honeycombs, provided that they have the aforementioned porosity and pore size characteristics. The open cells of a metal foam preferably range from about 20 pores per inch (ppi) to about 3000 ppi and more preferably about 40 to about 600 ppi. PPI is defined as the largest number of pores per inch (in isotropic materials the direction of the measurement is irrelevant; however, in anisotropic materials, the measurement is done in the direction that maximizes pore number). In the present invention, ppi is measured by scanning electron microscopy. It has been discovered that a porous support provides several advantages in the present invention including low pressure drop, enhanced thermal conductivity over conventional ceramic pellet supports, and ease of loading/unloading in chemical reactors.

The buffer layer 102, if present, has different composition and/or density than both the support and the interfacial layers, and preferably has a coefficient of thermal expansion that is intermediate to the thermal expansion coefficients of the porous support and the interfacial layer. Preferably, the buffer layer is a metal oxide or metal carbide. Applicants discovered that vapor-deposited layers are superior because they exhibit better adhesion and resist flaking even after several thermal cycles. More preferably, the buffer layer is $Al_2O_3$, $TiO_2$, $SiO_2$, and $ZrO_2$ or combinations thereof. More specifically, the $Al_2O_3$ is $\alpha$-$Al_2O_3$, $\gamma Al_2O_3$ and combinations thereof. $\alpha$-$Al_2O_3$ is more preferred because of its excellent resistance to oxygen diffusion. Therefore, it is expected that resistance against high temperature oxidation can be improved with alumina coated on the porous support 100. The buffer layer may also be formed of two or more compositionally different sublayers. When the porous support 100 is metal, for example a stainless steel foam, a preferred embodiment has a buffer layer 102 formed of two compositionally different sub-layers (not shown). The first sublayer (in contact with the porous support 100) is preferably $TiO_2$ because it exhibits good adhesion to the porous metal support 100. The second sublayer is preferably $\alpha$-$Al_2O_3$ which is placed upon the $TiO_2$. In a preferred embodiment, the $\alpha$-$Al_2O_3$ sublayer is a dense layer that provides excellent protection of the underlying metal surface. A less dense, high surface area alumina interfacial layer may then be deposited as support for a catalytically active layer.

Typically the porous support 100 has a thermal coefficient of expansion different from that of the interfacial layer 104. Accordingly, for high temperature catalysis (T>150° C.) a buffer layer 102 can be used to transition between two coefficients of thermal expansion. The thermal expansion coefficient of the buffer layer can be tailored by controlling the composition to obtain an expansion coefficient that is compatible with the expansion coefficients of the porous support and interfacial layers. Another advantage of the buffer layer 102 is that it provides resistance against side reactions such as coking or cracking caused by a bare metal foam surface. For chemical reactions which do not require large surface area supports such as catalytic combustion, the buffer layer 102 stabilizes the catalyst metal due to strong metal to metal-oxide interaction. In chemical reactions which require large surface area supports, the buffer layer 102 provides stronger bonding to the high surface area interfacial layer 104. Preferably, the buffer layer is free of openings and pin holes—this provides superior protection of the underlying support. More preferably, the buffer layer is nonporous. The buffer layer has a thickness that is less than one half of the average pore size of the porous support. Preferably, the buffer layer is between about 0.05 and about 10 $\mu$m thick, more preferably, less than 5 $\mu$m thick. The buffer layer should exhibit thermal and chemical stability at elevated temperatures.

In some embodiments of the present invention, adequate adhesion and chemical stability can be obtained without a buffer layer, so the buffer layer can be omitted, thus saving cost, providing extra volume and further enhancing heat transfer from the catalyst.

The interfacial layer 104 can be comprised of nitrides, carbides, sulfides, halides, metal oxides, carbon and combinations thereof. The interfacial layer provides high surface area and/or provides a desirable catalyst-support interaction for supported catalysts. The interfacial layer can be comprised of any material that is conventionally used as a catalyst support. Preferably, the interfacial layer is a metal oxide. Examples of metal oxides include, but are not limited, to $\gamma$-$Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer 104 may serve as a catalytically active layer without any further catalytically active material deposited thereon. Usually, however, the interfacial layer 104 is used in combination with catalytically active layer 106. The interfacial layer may also be formed of two or more compositionally different sublayers. The interfacial layer has a thickness that is less than one half of the average pore size of the porous support. Preferably, the interfacial layer thickness ranges from about 0.5 to about 100 $\mu$m, more preferably from about 1 to about 50 $\mu$m. The interfacial layer can be either crystalline or amorphous and preferably has a BET surface area of at least 1 $m^2/g$.

The catalytically active material 106 (when present) can be deposited on the interfacial layer 104. Alternatively, a catalytically active material can be simultaneously deposited with the interfacial layer. The catalytically active layer (when present) is typically intimately dispersed on the interfacial layer. That the catalytically active layer is "disposed on" or "deposited on" the interfacial layer includes the conventional understanding that microscopic catalytically active particles are dispersed: on the support layer (i.e., interfacial layer) surface, in crevices in the support layer, and in open pores in the support layer. The present invention employs a Fischer-Tropsch catalytic metal in the catalytically active layer. Conventional Fischer-Tropsch catalysts are based on iron (Fe), cobalt (Co), nickel (Ni), ruthenium (Ru), rhenium (Re), osmium (Os) and combinations thereof. Catalytic metals in the present invention are preferably iron, cobalt, ruthenium, rhenium, osmium and combinations thereof. In addition to these catalyst metals, a promoter may be added. Promoters could include transition metals and metal oxides (except Au and Hg), lanthanide metals or metal oxides, and group IA elements (except H). A Fischer-Tropsch catalytic metal combined with a suitable support such as the porous support with inter-facial layer described herein is termed a supported Fischer-Tropsch catalytic metal. In less preferred embodiments, the supported Fischer-Tropsch catalytic metal can be a Fischer-Tropsch catalytic metal supported on other supports such as a powder.

In order to mitigate the mass transfer limitation of the catalyst structure, the catalyst impregnation preferably forms a porous interfacial layer having a depth less than 50 $\mu$m, preferably less than 20 $\mu$m. Therefore, the diffusion path length is at least a factor of 5 shorter than for standard catalyst particles. The thinner impregnated catalyst structure also enhances heat transfer, due to a shorter heat transfer pathway, and leads to lower selectivity to $CH_4$.

The catalyst structure may be any geometric configuration. Preferably, the catalyst is a porous structure such as a foam, felt, wad and combinations thereof. The catalyst (including the support and Fischer-Tropsch catalytic metal) preferably is sized to fit within a reaction chamber. The catalyst may be a single piece of porous contiguous material, or many pieces in physical contact. The catalyst is preferred to have contiguous material and contiguous porosity such that molecules can diffuse through the catalyst. In this preferred embodiment, the catalyst can be disposed in a reaction chamber such that gases will flow substantially through the catalyst (single or multiple pieces) rather than around it. In a preferred embodiment, the cross-sectional area of the catalyst occupies at least 80%, more preferably at least 95% of the cross-sectional area of the reaction chamber. In preferred embodiments, the catalytically active metal is distributed on surfaces throughout catalyst such that reactants passing through the catalyst can react anywhere along the passage through the catalyst; this is a significant advantage over pellet-type catalysts that have a large volume of unused space or catalytically ineffectively used space in the pellet's interior. The porous catalyst is also superior over powders because packed powders may cause a severe pressure drop. The catalyst preferably has a surface area, as measured by BET, of greater than about 0.5 $m^2/g$, more preferably greater than about 2.0 $m^2/g$.

In addition, because the catalyst structure is not required to be attrition resistant as would be with the catalyst particles used in a fluidized bed reactor, greater porosity may be used, for example porosity greater than about 30%, thus, enhancing mass transfer in the catalyst structure.

Catalysts of the present invention can also be characterized by the properties they exhibit. Factors that can be controlled to effect these properties include: selection of the porous support, buffer, interfacial, and catalytically active layers; gradation of thermal expansion coefficients, crystallinity, metal-support interactions, catalyst size, thermal conductivity of the support, porosity, thermal conductance from reaction chamber, deposition techniques and other factors as are apparent in view of the descriptions herein. Certain preferred embodiments of the catalysts of the present invention exhibit one or more of the following properties: adhesion—after 3 thermal cycles in air, the catalyst exhibits less than 2% (by area) of flaking as viewed by SEM (scanning electron microscope) analysis; oxidation resistance, conversion of carbon monoxide, contact times, methane selectivity, pressure drop and production rates.

Oxidation resistance can be measured by thermal gravity analysis (TGA). After heating at 580° C. in air for 2500 minutes, the catalyst increases in weight by less than 5%, more preferably less than 3%; still more preferably, after heating at 750° C. in air for 1500 minutes, the catalyst increases in weight by less than 0.5%. Each thermal cycle consists of heating from room temperature to 600° C. in air at a heating rate of 10° C./min, maintaining the temperature at 600° C. for 3000 minutes, and cooling at a rate of 10° C./min.

Another aspect of the present invention is a catalyst and method utilizing the catalyst that provides lower methane selectivity at lower pressures. It was unexpectedly discovered that by using the porous catalyst structure of the present invention, reducing the pressure of the Fischer-Tropsch reaction resulted in increased yield, less selectivity toward methane. See Example 2.

Enhanced heat transfer in the present invention enables short contact times, good conversion, and low methane selectivities. Various factors that can be used to enhance heat transfer include: use of a metal support, preferably a porous metal support such as a metal foam or wad, thin buffer (if present) and interfacial layers, a heat exchanger in thermal contact with the reaction chamber, microchannels in reaction chamber and/or heat exchanger, and a catalyst that has a thickness in the direction of heat transfer (e.g., the direction to the reaction chamber walls and substantially perpendicular to the direction of flow) of about 1.5 cm or less, more preferably about 1 to 10 mm, and still more preferably about 1 to 3 mm.

The invention further provides apparatusses (i.e., reactors) and methods for hydrogenating carbon monoxide. In a preferred embodiment, the catalytic process is conducted in apparatus having microchannels. A microchannel has a characteristic dimension less than about 1 mm. In one embodiment, the reaction chamber has walls defining at least one microchannel through which pass reactants into the reaction chamber. In a preferred embodiment, the reaction chamber walls separate the reaction chamber from at least one cooling chamber. Examples of suitable microchannel apparatus and various process related factors are described in U.S. Pat. Nos. 5,611,214, 5,811,062, 5,534,328, 6,129,973, 6,192,596, 6,200,536 and U.S. patent applications Ser. Nos. 09/123,779, and 09/375,614 (filed Aug. 17, 1999), all of which are incorporated by reference as if reproduced in full below. In another preferred embodiment, the catalyst is a monolith—a single contiguous, yet porous, piece of catalyst or several contiguous pieces that are stacked together (not a bed of packed powder or pellets or a coating on the wall of a microchannel) that can easily be inserted and extracted from a reaction chamber. The piece or stack of catalyst pieces preferably have a width of 0.1 mm to about 2 cm, with a preferred thickness of less than about 1.5 cm, more preferably less than about 1.0 cm, and still more preferably, about 1 to about 3 mm. The inventive catalyst may provide numerous advantages to catalytic processes such as: chemical stability, stability to repeated thermal cycling, thermal stability, efficient loading and unloading of catalysts, high rates of heat transfer and mass transfer, and maintenance of desired catalytic activity.

The metal surfaces within microchannel apparatus can be coated with either or both the buffer and the interfacial layers. This can be done using any of the processes described herein, preferably by vapor deposition. Preferred coating materials include titania and and 5–10% $SiO_2/Al_2O_3$. The interior surfaces of the reaction chamber, heat exchanger and other surfaces of microchannel apparatus may be coated. In some embodiments, the walls of a reaction chamber can be coated with an optional buffer layer, an interfacial layer, and a catalytically active material—typically the catalytically active material and the interfacial layer combine to form a supported catalyst. Coatings can also be applied to metal walls in tubes and pipes that form connections to or within microchannel apparatus.

According a preferred method of the present invention, residence time less than 5 seconds can be achieved by: (a) providing a catalyst structure of a metal foam having a catalyst thereon; and (b) passing a feed stream having a mixture of hydrogen gas with carbon monoxide gas through the catalyst structure and heating the catalyst structure to at least 200° C., thereby obtaining a product stream of at least 25% conversion of carbon monoxide, and at most 25% selectivity toward methane. In another preferred method, the catalyst structure includes a buffer layer and an interfacial layer with a catalytically active metal disposed on the interfacial layer.

The present invention provides processes for hydrogenating carbon monoxide. In preferred processes, the ratio of hydrogen to carbon monoxide ranges from about 1:1 to about 6:1, preferably from about 2:1 to about 3.5:1. Hydrogenation is preferably conducted at temperatures above about 200° C., more preferably between about 200° C. and about 300° C., and still more preferably between about 200° C. and about 270° C.

Certain embodiments of the present invention can be characterized in terms of residence or contact time. These terms have well-defined meanings in the art. Contact time is the total volume of the catalyst chambers divided by the total flowrate of inlet reactants assuming they are an ideal gas corrected to standard conditions (i.e., the volume of the catalyst chamber/F-total at STP where STP is 273 K and 1 atm). The volume of the catalyst chambers includes the volume in immediate proximity and surrounding the catalyst zone. As an example, if one were to pack one quarter of the channels with powders, then the volume of the catalyst chamber would only include that region where gas can flow and where it can contact the catalyst, i.e. only one quarter of the total channel volume would be included in this calculation. The volume of dead space, i.e., headers, footers, etc. is ignored in this calculation. Average residence time (also referred to as residence time) is the total volume of the catalyst chambers divided by the total flowrate of inlet reactants, corrected to the actual temperature and pressure of the reactants in the reactor (i.e., the volume of the catalyst chamber/F-total corrected to actual conditions). F-total at STP is the total volumetric flowrate of reactants (includes all reactants, and diluents if present). Inlet gases are typically metered with mass flow controllers set to standard conditions, i.e. the user presets the desired STP flowrate. F-total corrected to actual conditions=F-total-STP× (Temperature in K)/273×1 atm/(P actual in atm): this value is used to calculate the residence time or the 'true time' within a reactor. Most practitioners prefer to use contact time, because it is a convenient method to keep the time variable fixed while stepping through 10 degree C. increments in reaction temperature etc.

Contact times less than 5 seconds may be accomplished with standard equipment but at the expense of significant energy to raise the space velocity of the reactants to overcome the pressure drop and poorer heat transfer leading to higher methane formation. Thus, the inventive method is preferably carried out in a reaction chamber in which the catalyst has a thickness of about 1.5 cm or less and is touching or in close proximity (within about 1 mm) of a reaction chamber wall, where the reaction chamber wall is in thermal contact with a heat exchanger. Heat transfer from the reaction chamber is preferably enhanced by addition of microchannels on at least one reaction chamber wall on the side of the reaction chamber wall opposite the catalyst structure. The catalyst preferably has contiguous and relatively large pores, such as in a foam, to avoid large pressure drops. Preferably the pore size of the large pores in the catalyst is between about 10 $\mu$m and about 300 $\mu$m.

In preferred embodiments of the present invention, carbon monoxide hydrogenation is conducted at a contact time of less than 5 seconds, more preferably, less than about 2 seconds and still more preferably between about 0.1 and about 1 seconds. At these contact times, good CO conversion and low methane selectivity can be obtained. Preferably, CO conversion is at least 25%, more preferably, at least 50%, and still more preferably, greater than about 80%. Methane selectivity is preferably less than 25%, more preferably less than about 20%, and still more preferably, between about 15% and 5%. Additionally, these properties can be achieved with low pressure drops across the reaction chamber. In the present invention, the pressure drop through the reaction chamber is preferably less than about 15 psig, more preferably less than 10 psig, still more preferably less than about 5 psig, and yet more preferably less than about 1 psig.

A method of making the inventive catalyst has the steps of selecting a porous support 100, optionally depositing a buffer layer 102 on the porous support 100 and depositing an interfacial layer 104 thereover. Optionally a catalyst layer 106 may be deposited onto the interfacial layer 104 or both the interfacial layer and the catalyst layer may be simultaneously deposited on the buffer layer 102.

Because metal has web surfaces that are nonporous and smooth, deposition of a buffer layer or interfacial layer may be impeded. One way to mitigate this problem is to rough the metal surface via chemical etching. The adhesion of high surface area supported metal catalysts, such as gamma-alumina, to metal foam is significantly improved when metal foam is roughed via chemical etching using mineral acid solutions, for example 0.1 to 1 M HCl. Roughed web surface also shows improved resistance to the spalling of catalyst layer under thermal cyclings. In a preferred embodiment, wherein a metal foam is used as the porous support 100, the metal foam is etched prior to vapor depositing the buffer layer 102. Etching is preferably with an acid, for example HCl.

Deposition of the buffer layer 102 is preferably by vapor deposition including but not limited to chemical vapor deposition, physical vapor deposition or combinations thereof. Surprisingly, it has been found that vapor deposition, which is typically conducted at high temperatures, results in polycrystalline or amorphous phases that provide good adhesion of the buffer layer to the surface of the porous support. The method is particularly advantageous for adhering a metal oxide buffer layer to a metal porous support. Alternatively, the buffer layer 102 may be obtained by solution coating. For example, the solution coating has the steps of metal surface functionalization via exposing the metal surface to water vapor to form surface hydroxyls, followed by surface reaction and hydrolysis of alkoxides to obtain a coating of metal oxide. This solution coating may be preferred as a lower cost method of depositing the buffer layer 102.

The interfacial layer 104 is preferably formed by vapor or solution deposition using precursors as are known for these techniques. Suitable precursors include organometallic compounds, halides, carbonyls, acetonates, acetates, metals, colloidal dispersions of metal oxides, nitrates, slurries, etc. For example, a porous alumina interfacial layer can be wash-coated with PQ alumina (Nyacol Products, Ashland, Mass.) colloidal dispersion followed by drying in a vacuum oven overnight and calcining at 500° C. for 2 hours.

The catalytically active material can be deposited by any suitable method For example, catalytic metal precursors can be depoited on colloidal metal oxide particles and slurry coated on a porous support, then dried and reduced.

EXAMPLE 1

The effect of residence time and reaction temperature on the catalytic conversion of CO with $H_2$ was examined in a constant flow reactor. The reactor was supplied with a mixture of feed gas, comprised of $H_2$ and CO in a molar, or volumetric (assuming ideal gas behavior), ratio of $H_2$/CO=3. This reactant feed was fed into a reaction chamber, which was maintained at a constant temperature inside an isothermal furnace. The interior of the catalyst chamber measures 35.6-mm (1.4-in) in length, 1.5-mm (0.060-in) in thickness and 8-mm (0.315-in) in width. The reaction products then exited the reaction chamber and were collected and analyzed for composition.

The catalyst for this experiment was prepared as follows. First, acidic gamma-alumina support powder (Strem) was ground and sieved to between 70- and 100-mesh (150 to 220-micron), and calcined (stabilized) at 500° C. for several hours. This powder was then impregnated with a solution containing cobalt nitrate hexahydrate and ruthenium trichloride hydrate (or ruthenium nitrosyl nitrate) precursors, present in desired concentrations as to produce a 15-wt % cobalt, 1-wt % ruthenium on alumina catalyst. The precursor solution was prepared in such a manner as to saturate the pore volume of the alumina support without over saturation of the alumina support. This powder was then dried in a vacuum oven at 100° C. for at least 4-hours, followed by drying at 100° C. for at least 12-hours. The powder was then calcined by heating at 350° C. for at least 3-hours. A portion of the powder was then combined with distilled water in a water-to-catalyst weight ratio of at least 2.5 to produce a catalyst slurry. This catalyst slurry is then placed in a container with inert grinding media balls and placed on a rotating device for at least 24-hours. This slurry was then ready to coat a pre-treated metal foam monolith type support. The metal foam support monolith is typically 80-ppi (pores per inch) stainless steel (supplied by AstroMet, Cincinnati, Ohio), with characteristic macropores on the order of about 200- to 250-$\mu$m, and with a porosity of about 90% (by volume). The monolith pretreatment consists of cleaning successively in dichloromethane and acetone solvents in a water bath submersed in a sonication device to agitate the solvent within the monolith. Optionally, the metal surface of the monolith may then be roughened by etching with acid. If this is desired, the monolith is submerged in 0.1-molar nitric acid, and placed in a sonication device. The monolith was then rinsed in distilled water and dried at about 100° C. The monolith was then coated with a layer of alumina using a chemical vapor deposition (CVD) technique. The CVD system has a horizontal, hot-wall reactor with three precursor sources. The CVD coatings are performed at a deposition temperature of 600° C. and reactor pressure of 5-torr. Aluminum iso-propoxide was used as the aluminum precursor. This precursor is stored in a quartz container maintained at 100° C. during deposition, which produces a vapor that is carried into the CVD reactor by a flow of nitrogen carrier gas for about 20-minutes. Air was then used to oxidize the aluminum precursor to alumina. Typical thickness of the alumina coatings is about 0.5-$\mu$m. This pretreated metal support foam monolith was then coated with the catalyst slurry by dip coating. The monolith was then dried in flowing air or nitrogen at room temperature while continuously rotating the monolith in such a way as to create a uniform coverage of the dried catalyst slurry layer. The monolith was then dried at 90° C. for at least 1-hour, heated slowly to 120° C. over the course of at least-hour, dried further at 120° C. for at least 2-hours, and then heated to 350° C. and calcined for at least 3-hours. Typically, 0.1–0.25 g of alumina supported Co—Ru powder catalyst was coated on the metal foam monolith with dimensions and characteristics aforementioned.

The catalyst monolith or powder, weighing approximately 0.5 grams was then placed inside the reaction chamber and activated (or reduced) prior to reaction by heating to about 350° C. to 400° C. and under flow of a hydrogen-containing stream of about 10- to 20-% (by mole or volume) hydrogen in an inert carrier gas (such as nitrogen or helium) at a flow rate of at least 20 cc/min (measured at 273 K and 1-atm) for at least 2-hours. The catalyst was then allowed to cool to reaction temperatures, at least 200° C. The catalyst was then exposed to a feed gas comprised of $H_2$ and CO in a desired ratio of moles of $H_2$ per mole of CO. The feed gas flow rate is controllable to allow for precise generation of a desired contact time, usually about 1-second. The reaction products were then analyzed to evaluate the conversion of CO and the selectivity towards certain products, such as methane. The reaction was conducted at pressures up to 24-atmospheres (about 353-psia).

Table E1-1 shows the results of these experiments. In general, the powder form of the catalyst produced greater conversions at a given temperature than the monolithic form. However, at a given temperature, the monolith catalyst produced less methane. In conventional Fischer-Tropsch reactors, methane formation is predominately affected by reactor temperature and feed composition, although it is also affected to a lesser extent by other parameters, such as contact time. The fact that the monolithic catalyst yields lower methane selectivity at a given temperature suggests that the monolith is better able to conduct heat away from the inner part of the reactor, and thus avoid higher local temperatures, which are often present in the inner sections of packed or powder beds. For the monolithic catalyst, conversion is a strong function of both temperature and contact time, and conversion will increase with increasing temperature and/or time. Decreasing the contact time from 2-seconds to 1-sec at 275° C. for the monolithic catalysts resulted in lower conversion and higher methane selectivity.

When compared to the results of previous studies in Table 1, several characteristics are apparent:

compared to all of these references, sufficient catalyst performance (conversion greater than about 50% and methane selectivity below about 25%) can be achieved at a contact time that is about three- to twelve-times shorter formation of methane, which is highly favored at high reactor temperatures and the hydrogen-to-carbon feed ratios, is intermediate to references 1 and 3, which utilize the most similar contact times; however, the monolithic catalyst produces comparable methane selectivities under conditions which are much more unfavorable than used in these references. The monolith form was able to produce this amount of methane at temperatures up to 260° C. (compared to 240° C. in reference 1) and a $H_2$-to CO feed ratio of 3 (compared to 2 for references 1 and 3). This further shows that the monolithic form removes heat more effectively that powder or pellet forms, and that methane formation can be suppressed, even under undesirable conditions.

at a comparable $H_2$-to-CO feed ratio of 3 and CO conversion (about 80%), the powdered catalyst in reference 7 produces much higher selectivity to methane than the inventive catalyst even at lower temperatures and longer contact times, where methane formation is unfavored. Note that in reference 7, a change in $H_2$-to-CO feed ratio of from 2 to 3 nearly tripled methane selectivity.

In addition, the thickness of the catalyst layer in the monolith (typically less than 20-$\mu$m) is much less than finest particle size used either in fixed bed reactors (>100 $\mu$m), or slurry type or fluidized type reactors (>50-$\mu$m). Therefore, the internal mass transfer diffusion pathway is shorter in the monolith catalyst. Moreover, under Fischer-Tropsch synthesis operations, internal pores within the catalyst are normally filled with hydrocarbon products, and hydrogen has much higher diffusivities than that of CO. This could result in much higher $H_2$/CO ratio inside a pellet or powder catalyst than that in the bulk feed, which favors methanation. Therefore, the thinner catalyst layer with the monolith catalyst will result in a relatively lower local $H_2$ concentration within the catalyst to minimize the selectivity to methane. Yet another advantage of porous catalysts is their efficient use of space in which molecules can pass through and react inside the catalyst, without causing excessive pressure drops.

TABLE E1-1

Fischer-Tropsch Catalyst Performance

| Catalyst | Conditions | Contact time | Convrsion | $CH_4$ selectivity |
|---|---|---|---|---|
| Co-Ru/$Al_2O_3$/ foam | 231° C., 24-atm, $H_2$/CO = 3 | 1-sec | 17% | 9.6% |
| Co-Ru/$Al_2O_3$/ foam | 247° C., 24-atm, $H_2$/CO = 3 | 1-sec | 29% | 15% |
| Co-Ru/$Al_2O_3$/ foam | 264° C., 24-atm, $H_2$/CO = 3 | 1-sec | 50% | 22% |

TABLE E1-1-continued

Fischer-Tropsch Catalyst Performance

| Catalyst | Conditions | Contact time | Convrsion | $CH_4$ selectivity |
|---|---|---|---|---|
| Co-Ru/$Al_2O_3$/foam | 264° C., 24-atm, $H_2$/CO = 3 | 1-sec | 49% | 22% |
| Co-Ru/$Al_2O_3$/foam | 275° C., 24-atm, $H_2$/CO = 3 | 1-sec | 69% | 24% |
| Co-Ru/$Al_2O_3$/foam | 275° C., 24-atm, $H_2$/CO = 3 | 2-sec | 84% | 9.0% |
| Co-Ru/$Al_2O_3$/foam | 245° C., 24-atm, $H_2$/CO = 3 | 1-sec | 33% | 12% |
| Co-Ru/$Al_2O_3$/powder | 245° C., 24-atm, $H_2$/CO = 3 | 1-sec | 99.6% | 36% |

EXAMPLE 2

An experiment was conducted to demonstrate operation at various pressures. The equipment was the same as in Example 1.

According to the literature, variation in pressure should only affect true residence time in Fischer-Tropsch synthesis. In other words, conventional wisdom in Fischer-Tropsch reactions is that reaction rate is proportional to pressure under identical residence time. However, as shown in Table E2-1, with the catalyst structure of the present invention, catalyst activity was unexpectedly enhanced as the pressure was decreased under the same residence time. This surprising result is attributed to the enhanced mass and heat transfer possible with the catalyst structure of the present invention.

TABLE E2-1

Engineered catalyst performance for Fischer-Tropsch synthesis at about 250° C. under a constant residence time (i.e., temperature and pressure corrected contact time) of 12.5 seconds. The contact time at 24 atm (absolute) is 1 sec.

| Pressure, atm (absolute) | Conversion, % | Selectivity to $CH_4$, % |
|---|---|---|
| 6 | 63 | 18 |
| 7 | 41 | 22 |
| 11 | 34 | 19 |
| 24 | 24 | 26 |

EXAMPLE 3

Use of acidic gamma alumina supported Co or Ru alone as a catalyst on the metal foam was also tested under the conditions of Example 1 and performance was found to be worse than that of bimetallic catalyst such as Co—Ru.

EXAMPLE 4

An experiment was conducted to demonstrate certain advantages of the buffer layer of the present invention.

An unetched stainless steel foam (Astromet, Cincinnati Ohio) was coated with 1000 Angstroms $TiO_2$ via chemical vapor deposition. Titanium isopropxide (Strem Chemical, Newburyport, Mass.) was vapor deposited at a temperature ranging from 250 to 800° C. at a pressure of 0.1 to 100 torr. Titania coatings with excellent adhesion to the foam were obtained at a deposition temperature of 600° C. and a reactor pressure of 3 torr.

SEM (scanning electron microscope) analysis showed that the stainless steel foam supported gamma-alumina with a $TiO_2$ buffer layer did not show spalling after several (3) thermal cycles from room temperature to 600° C. In a control experiment with a stainless steel foam support coated with gamma-alumina without the $TiO_2$ buffer layer, severe flaking or spalling of the gamma alumina under the identical testing conditions was observed. The uncoated steel foam rapidly oxidized when heated to 500° C. in air (as shown by the weight gain, i.e., thermal gravity, values) while the titania coated steel oxidized relatively slowly. Similarly, uncoated nickel foam oxidized, while, under the same conditions (heating to 500° C. or 750° C. in air), the titania coated nickel foam showed zero (i.e., undetectable levels of) oxidation.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of Fischer-Tropsch reaction, comprising the steps of:

(a) providing a catalyst structure comprising a porous support with a first pore surface area and a first pore size of at least about 0.1 µm;

a buffer layer disposed on said porous support;

a porous interfacial layer with a second pore surface area and a second pore size less than said first pore size, said porous interfacial layer disposed upon said buffer layer;

a Fischer-Tropsch catalyst placed upon said second pore surface area; and (b) passing a feed stream having a mixture of hydrogen gas with carbon monoxide gas through said catalyst structure and heating said catalyst structure to at least 200° C. at an operating pressure, said feed stream having a residence time within said catalyst structure less than 5 seconds, thereby obtaining a product stream of at least 25% conversion of carbon monoxide, and at most 25% selectivity to methane.

2. The method as recited in claim 1, wherein reducing the operating pressure has the effect of decreasing selectivity toward methane.

3. The method of claim 1 wherein said porous support is metal.

4. The method as recited in claim 3, wherein said heating is heating between 200 and 270° C.

5. The method as recited in claim 3, further comprising cooling with a cooling chamber in thermal contact with said catalyst structure.

6. The method of claim 1 wherein the catalyst structure has contiguous material and contiguous porosity such that molecules can diffuse through the catalyst, and the catalyst structure is disposed in a reaction chamber such that gases will flow substantially through the catalyst structure.

7. The method of claim 6 wherein the catalyst structure possesses catalytic activity such that, if the catalyst is placed inside an isothermal furnace and exposed to a feed stream consisting of a 3 to 1 ratio of hydrogen gas to carbon monoxide, at 250° C., at 6 atm, at a contact time less than 5 seconds and the product stream is collected and cooled to room temperature, the selectivity to methane is less than 25% and the carbon monoxide conversion is greater than 25%.

8. The method of claim 6 wherein the cross-sectional area of the catalyst structure occupies at least 80% of the cross-sectional area of the reaction chamber.

9. The method of claim 1 further comprising cooling with a cooling chamber in thermal contact with said catalyst structure.

10. The method of claim 9 wherein the cooling chamber comprises a microchannel.

11. The method of claim 9 wherein the Fischer-Tropsch catalyst is selected from the group consisting of cobalt, ruthenium, iron, rhenium, nickel, osmium and combinations thereof.

12. The method of claim 9 wherein the Fischer-Tropsch catalyst is selected from the group consisting of cobalt, ruthenium, iron, rhenium, osmium and combinations thereof; and wherein the porous structure comprises a honeycomb, felt, foam or wad.

* * * * *

(12) EX PARTE REEXAMINATION CERTIFICATE (8327th)
United States Patent
Wang et al.

(10) Number: US 6,750,258 C1
(45) Certificate Issued: Jun. 14, 2011

(54) CATALYST STRUCTURE AND METHOD OF FISCHER-TROPSCH SYNTHESIS

(75) Inventors: Yong Wang, Richland, WA (US); David P. Vanderwiel, Richland, WA (US); Anna Lee Y. Tonkovich, Pasco, WA (US); Yufei Gao, Kennewick, WA (US); Eddie G. Baker, Pasco, WA (US)

(73) Assignee: Battelle Memorial Institute K1-53, Richland, WA (US)

Reexamination Request:
No. 90/011,108, Jul. 23, 2010

Reexamination Certificate for:
Patent No.: 6,750,258
Issued: Jun. 15, 2004
Appl. No.: 10/282,554
Filed: Oct. 28, 2002

Related U.S. Application Data

(60) Division of application No. 09/492,245, filed on Jan. 27, 2000, now Pat. No. 6,491,880, which is a continuation-in-part of application No. 09/375,610, filed on Aug. 17, 1999, now Pat. No. 6,451,864.

(51) Int. Cl.
*B01J 19/24* (2006.01)
*B01J 8/02* (2006.01)
*B01J 23/89* (2006.01)
*B01J 12/00* (2006.01)
*B01J 35/00* (2006.01)
*B01J 37/00* (2006.01)
*B01J 35/10* (2006.01)
*C07C 1/04* (2006.01)
*C07C 1/00* (2006.01)
*C10G 2/00* (2006.01)

(52) U.S. Cl. .................................. 518/715; 518/700
(58) Field of Classification Search .................. None
See application file for complete search history.

(56) References Cited

U.S. PATENT DOCUMENTS 3,972,837 A   8/1976   Acres et al.

FOREIGN PATENT DOCUMENTS

WO   WO 98/38147 A1   9/1998

OTHER PUBLICATIONS

"Design, synthesis, and use of cobalt–based Fischer–Tropsch synthesis catalysts," Enrique Iglesia, Applied Catalysis (1997).

*Primary Examiner*—Krisanne Jastrzab

(57) ABSTRACT

The present invention includes Fischer-Tropsch catalysts, reactions using Fischer-Tropsch catalysts, methods of making Fischer-Tropsch catalysts, processes of hydrogenating carbon monoxide, and fuels made using these processes. The invention provides the ability to hydrogenate carbon monoxide with low contact times, good conversion rates and low methane selectivities. In a preferred method, the catalyst is made using a metal foam support.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 1 is confirmed.

Claims 2-12 were not reexamined.

\* \* \* \* \*